United States Patent [19]
Takamizawa et al.

[11] 4,243,607
[45] Jan. 6, 1981

[54] PROCESS FOR THE PREPARATION OF TETRACHLOROALKANES

[75] Inventors: Minoru Takamizawa; Haruo Okamoto; Mitsuo Umemura; Kazuo Kooya, all of Annaka, Japan

[73] Assignee: Shin-Etsu Chemical Co. Ltd., Tokyo, Japan

[21] Appl. No.: 739,049

[22] Filed: Nov. 5, 1976

[30] Foreign Application Priority Data

Nov. 10, 1975 [JP] Japan ................. 50/134902

[51] Int. Cl.$^3$ ............................. C07C 17/28
[52] U.S. Cl. ................................. 570/257
[58] Field of Search ........................ 260/658 C

[56] References Cited

U.S. PATENT DOCUMENTS

| 3,454,657 | 7/1969 | Decker et al. | 260/658 C |
| 3,631,115 | 12/1971 | Nakagawa et al. | 260/658 C |
| 3,651,019 | 3/1972 | Asscher et al. | 260/658 C |

FOREIGN PATENT DOCUMENTS 1146463  3/1969  United Kingdom ............. 260/658 C

OTHER PUBLICATIONS

Asahara et al., J. Japan Chem. Soc., vol. 74, pp. 703–705, (1970) (see Chem. Abs., vol. 75, 48334N (1971)).

*Primary Examiner*—Delbert E. Gantz
*Assistant Examiner*—Joseph A. Boska
*Attorney, Agent, or Firm*—Toren, McGeady and Stanger

[57] ABSTRACT

An ethylenic hydrocarbon is reacted with carbon tetrachloride in the presence of an alkyl phosphite, an iron chloride and a nitrile compound. According to this process, tetrachloroalkanes having more than two carbon atoms can be obtained in high yields.

11 Claims, No Drawings

PROCESS FOR THE PREPARATION OF TETRACHLOROALKANES

BACKGROUND OF THE INVENTION

The present invention relates to an improvement in the process for preparing tetrachloroalkanes from ethylenic hydrocarbons and carbon tetrachloride.

In the preparation of a tetrachloroalkane having more than two carbon atoms from an ethylenic hydrocarbon and carbon tetrachloride, various catalysts for carrying out the reaction in an advantageous manner have been proposed. The methods using the proposed catalysts, however, have merits and demerits, and no satisfactory method has heretofore been developed.

The conventional methods include, for example, (a) a method using an organic peroxide, such as, benzoyl peroxide and di-tertiary-butyl peroxide or an azo compound, such as azobisisobutyronotrile as, disclosed in U.S. Pat. No. 2,440,800, (b) a method using at least one member selected from organic or inorganic salts of metals and amines, optionally in combination with ammonia, metallic iron, EDTA and the like as disclosed in U.S. Pat. Nos. 3,213,149, 3,454,657, 3,651,019 and 3,462,503, (c) a method using a metal carbonyl compound as disclosed in U.S. Pat. No. 3,471,579, and (d) a method using triethyl phosphite and iron chloride in combination as disclosed in Chemical Abstracts, Vol. 75, 1971, 48334n.

The method (a) above is defective in that, since the reaction proceeds very violently and is extremely exothermic, special modifications of the reaction operation and apparatus must be effected so as to have the reaction rate controlled. Even though such modifications have been made, it sometimes is impossible to control the violent reaction, which involves the danger of explosion.

According to method (b), the yield of the product is low especially when the reaction is carried out under a relatively low pressure. Therefore, this method is impractical from the commercial point of view.

The catalyst used in method (c) is toxic and very expensive, and unsuitable for use in large quantities on commercial scale.

The catalyst used in method (d) is very poor in miscibility with carbon tetrachloride, and large quantities of tar-like substances are formed as by-products in the reaction. The tar-like by-products tend to adhere to the inner walls of a reaction vessel or pipings. Therefore, the method is disadvantageous especially when a continuous process is intended for conducting the reaction.

SUMMARY OF THE INVENTION

As the result of research conducted on the process for preparing tetrachloroalkanes from ethylenic hydrocarbons and carbon tetrachloride, it has been discovered that the use of an alkyl phosphite, an iron chloride and a nitrile compound in combination as the catalyst is capable of producing the desired tetrachloroalkanes with ease in high yields and without the disadvantages encountered in the conventional methods (a) to (d). Based on this finding, the inventors have succeeded in completing the present invention.

More specifically, in accordance with the present invention, there is provided a process for the preparation of tetrachloroalkanes having more than two carbon atoms comprising reacting an ethylenic hydrocarbon with carbon tetrachloride in the presence of an alkyl phosphite, an iron chloride and a nitrile compound.

DETAILED DESCRIPTION OF THE INVENTION

Starting substances used in the process of the present invention are an ethylenic hydrocarbon and carbon tetrachloride.

Illustrative of the ethylenic hydrocarbons are ethylene, propylene, 1-butene, 1-hexene, 1-octene, 2-butene, 2-hexene, 2-octene and 3-hexene, and they are chosen according to the kinds of the tetrachloroalkanes to be obtained.

Carbon tetrachloride useful in the process of the present invention is not restrictive as to its quality, and commercially available material can be used without further purification.

As described hereinbefore, an alkyl phosphite, an iron chloride and a nitrile compound are used in combination as the catalyst in the process of the present invention. As the alkyl phosphites, which are esters of phosphorous acid with alcohols having preferably 4 or less carbon atoms in the molecule, there can be mentioned, for example, monomethyl, monoethyl, monopropyl, dimethyl, diethyl, dipropyl, trimethyl, triethyl, tripropyl and tributyl phosphites, among which triethyl phosphite is especially preferred. As the nitrile compounds, there can be mentioned, for example, acetonitrile, propionitrile, n-butyronitrile, benzonitrile and phenylacetonitrile. The nitrile compounds are preferably nitriles having 3 or less carbon atoms in the molecule or, more preferable, acetonitrile. The iron chloride used in combination with the alkyl phosphite and the nitrile compound is iron(II) chloride or iron(III) chloride. Such iron chloride can be not only anhydrous but also hydrated salts.

It has been found that a ternary catalyst obtained by adding a nitrile compound, such a acetonitrile, to a binary catalyst of an alkyl phosphite and iron chloride has further enhanced catalytic activities. Moreover, the ternary catalyst containing the nitrile compound has a good miscibility with carbon tetrachloride and can easily be dissolved in the mixed reactants, while the formation of tarry material can be reduced, thus avoiding problems that would otherwise have been incurred by the presence of such tarry material. Furthermore, the catalyst containing the nitrile compound has a high resistance to catalyst poisons. Generally, the activities of a combined catalyst of an alkyl phosphite, for example, triethyl phosphite and iron chloride are remarkably reduced by various catalyst poisons, such as amines. But, if a nitrile compound is further combined with the catalysts of this type, the activities of the resulting catalysts are hardly influenced by the catalyst poisons. Moreover, the nitrile compound-containing catalysts do not undergo the poisoning action of certain metals, for example, nickel and chromium.

The process of the present invention is practised by putting an ethylenic hydrocarbon and carbon tetrachloride as the starting materials and the above-described catalyst into a reaction vessel and then heating the mixture with agitation under pressure. The process may be carried out by either the batchwise or continuous system.

The mole ratio of the starting ethylenic hydrocarbon and carbon tetrachloride and the charge of these starting substances into the reaction vessel will now be described in the following.

When the starting ethylenic hydrocarbon is liquid, it is convenient that carbon tetrachloride is charged into the reaction vessel in an amount equal to or in excess over the stoichiometric amount together with the ethylenic hydrocarbon and the catalyst in order that the carbon tetrachloride serves as the reaction medium also. When, on the other hand, the starting ethylenic hydrocarbon is a gas, the carbon tetrachloride and the catalyst are first charged in the reaction vessel and then ethylenic hydrocarbon is blown into the reaction vessel so that the predetermined pressure inside the reaction vessel is attained. During the reaction, the introduction of the ethylenic hydrocarbon is continued to compensate for pressure decreases and maintain the predetermined presure in the reaction vessel.

It is preferred that the catalyst is charged in an amount such that the amount of the alkyl phosphite is from 0.1 to 10 mole %, preferably from 0.5 to 5.0 mole %, the amount of the iron chloride is from 0.01 to 1.0 mole %, preferably from 0.05 to 0.5 mole %, and the amount of the nitrile compound is from 0.1 to 10 mole %, preferably from 0.5 to 5.0 mole %, all based on the amount of carbon tetrachloride. These catalyst components may be charged into the reaction vessel severally or simultaneously in a prepared mixture.

In practical operation, it is preferred that in the reaction where the ethylenic hydrocarbon is ethylene or propylene, the temperature is between 80° and 150° C. and the pressure is between 5 and 20 kg/cm$^2$G. As the reaction pressure goes up higher, the reaction rate is enhanced but, on the other hand, higher tetrachloroalkanes are formed by the telomerization of ethylenic hydrocarbons in increased amounts. Because of this, it is advantageous to perform the reaction under a relatively low pressure, i.e., not exceeding 20 kg/cm$^2$G, insofar as the production of higher tetrachloroalkanes is not particularly intended.

The desired product can easily be isolated by distilling the reaction mixture to recover excessive carbon tetrachloride, and subjecting the remainder to fractional distillation.

In accordance with the process of the present invention, a violent exothermic reaction can easily be avoided and the formation of tar-like or resinous by-products is effectively prevented. Further, even though the reaction pressure is maintained at a level as low as about 10 kg/cm$^2$G, it is possible to obtain a reaction velocity sufficiently high from a practical standpoint. Further, according to the process of the present invention, the reaction can easily be carried out as a continuous process and the desired tetrachloroalkanes are obtained in high yields and at low costs.

Still further, the process of the present invention has an advantage in that the catalysts having a high toxicity, such as metal carbonyl compounds, can be dispensed with, and the catalysts suitable for use in the process of the present invention are inexpensive. Thus, the process of the present invention is advantageous from the industrial and commercial points of view.

The following examples illustrate the present invention.

EXAMPLE 1

A 1-liter capacity stainless steel autoclave equipped with a stirrer was charged with 800 g of carbon tetrachloride, 8.6 g of triethyl phosphite, 1.4 g of iron(III) chloride hexahydrate and 2.0 g of acetonitrile. Air inside the autoclave was replaced by nitrogen gas, and ethylene was then introduced under pressure so that the inside pressure increased to 5 kg/cm$^2$G.

The reaction mixture was heated up to 120° C. While the temperature was maintained at that temperature, ethylene was further pressured into the autoclave to increase the inside pressure to 10 kg/cm$^2$G. The reaction was continued for 6 hours, with ethylene further introduced to maintain the inside pressure at 10 kg/cm$^2$G.

When the reaction was over, the autoclave was cooled, and unreacted ethylene was purged. As a result, 952 g of a liquid reaction mixture was obtained, and from the mixture the following fractions were recovered by distillation.

Carbon tetrachloride—52 g
1,1,1,3-Tetrachloropropane—865 g
1,1,1,5-Tetrachloropentane—20 g
Other high-boiling substances—15 g Further, a similar procedure was repeated except that the pressure inside the autoclave under which the reaction was carried out was 5, 15 or 20 kg/cm$^2$G. instead of 10 kg/cm$^2$G. Each of the resultant reaction mixtures was found to contain 1,1,1,3-tetrachloropropane and 1,1,1,5-tetrachloropentane as follows.

| Reaction pressure | 1,1,1,3-Tetrachloropropane | 1,1,1,5-Tetrachloropentane |
|---|---|---|
| 5 kg/cm$^2$G | 39.3% | 1.0% |
| 15 kg/cm$^2$G | 92.4% | 4.3% |
| 20 kg/cm$^2$G | 92.6% | 6.8% |

EXAMPLE 2

A reaction was carried out in the same manner as in Example 1 with the reaction pressure of 10 kg/cm$^2$G except that propylene was used as the starting ethylenic hydrocarbon. As a result, 803 g of 1,1,1,3-tetrachlorobutane was obtained. The yield of this product based on the amount of carbon tetrachloride consumed was 94.7%.

EXAMPLE 3

The reaction was carried out in the same manner as in Example 1 with the reaction pressure of 10 kg/cm$^2$G except that diethylamine as a catalyst poison was added in an amount of 0.1% by weight based on carbon tetrachloride charged or a metal chloride which had been obtained by dissolving chips of 18-8 stainless steel in hydrochloric acid and evaporating the solution to dry was added in an amount of 0.05% by weight based on carbon tetrachloride charged. The content by weight % of 1,1,1,3-tetrachloropropane in each of the reaction mixtures thus obtained was determined, with the results shown below. For comparison, the same procedures as above were repeated except only that acetonitrile was omitted. The results of these comparative examples are also shown.

| Catalyst Poison | Present Invention | Comparative Example |
|---|---|---|
| Diethylamine | 93.7% | 71.4% |
| Metal chloride | 85.5% | 55.3% |
| None | 90.9% | 83.9% |

From the above test results, it is readily understood that the presence of an amine or metal chloride having catalyst poisoning activities in the reaction system of the process of the present invention does hardly affect the yields of product.

EXAMPLE 4

The reaction was carried out in the same manner as in Example 1 with the reaction pressure of 10 kg/cm$^2$G except that the alkyl phosphite was trimethyl phosphite, diethyl phosphite or tributyl phosphite instead of triethyl phosphite. The content of 1,1,1,3-tetrachloropropane in each of the reaction mixtures was as follows:
Trimethyl phosphite—66.5%
Diethyl phosphite—78.3%
Tributyl phosphite—49.1%

EXAMPLE 5

The reaction of Example 1 with the reaction pressure of 10 kg/cm$^2$G was repeated with the same amount of propionitrile instead of acetonitrile, to give a content of 1,1,1,3-tetrachloropropane 88.2% in the resultant reaction mixture.

EXAMPLE 6

The reaction of Example 1 with the reaction pressure of 10 kg/cm$^2$G was repeated with the same amount of anhydrous iron(III) chloride or iron(II) chloride tetrahydrate instead of iron(III) chloride hexahydrate, to give the content of 1,1,1,3-tetrachloropropane in the resultant reaction mixtures was 89.4% or 87.6%, respectively.

What is claimed is:

1. A process for the preparation of a tetrachloroalkane having more than two carbon atoms which comprises reacting an ethylenic hydrocarbon with carbon tetrachloride in the presence of a catalytically effective amount of a mixture composed of an alkyl phosphite, an iron chloride and a nitrile compound.

2. The process according to claim 1 wherein the ethylenic hydrocarbon is ethylene.

3. The process according to claim 1 wherein the ethylenic hydrocarbon is propylene.

4. The process according to claim 1 wherein the amount of the alkyl phosphite is from 0.1 to 10 mole %, the amount of the iron chloride is from 0.01 to 1.0 mole %, and the amount of the nitrile compound is from 0.1 to 10 mole %, each amount being based on carbon tetrachloride.

5. The process according to claim 1 wherein the alkyl phosphite is an ester of phosphorous acid with an alcohol having four or less carbon atoms in a molecule.

6. The process according to claim 1 wherein the alkyl phosphite is triethyl phosphite.

7. The process according to claim 1 wherein the nitrile compound is acetonitrile.

8. The process according to claim 1 wherein the reaction temperature is in the range of from 80° to 150° C.

9. The process according to claim 1 wherein the reaction pressure is in the range of from 5 to 20 kg/cm$^2$G.

10. A process for the preparation of 1,1,1,3-tetrachloropropane comprising reacting ethylene with carbon tetrachloride in the presence of triethyl phosphite, iron(III) chloride and acetonitrile.

11. A process for the preparation of a tetrachloroalkane having more than two carbon atoms which comprises reacting an ethylenic hydrocarbon selected from the group consisting of ethylene and propylene with carbon tetrachloride in the presence of a catalytically effective amount of a mixture composed of an alkyl phosphite, an iron chloride, and a nitrile selected from the group consisting of acetonitrile and propionic nitrile.

* * * * *